United States Patent [19]

Hefford et al.

[11] Patent Number: 4,943,430

[45] Date of Patent: Jul. 24, 1990

[54] TREATMENT OF KERATINOUS FIBRES

[75] Inventors: Robert J. W. Hefford; Andrew M. Murray, both of Cheshire, United Kingdom

[73] Assignee: Lever Brothers Company, New York, N.Y.

[21] Appl. No.: 358,467

[22] Filed: May 30, 1989

Related U.S. Application Data

[63] Continuation of Ser. No. 74,838, Jul. 17, 1987, abandoned.

[30] Foreign Application Priority Data

Jul. 30, 1986 [GB] United Kingdom ................. 8618634

[51] Int. Cl.$^5$ .......................... A61K 7/13; A61K 7/06
[52] U.S. Cl. .......................................... 424/70; 8/405; 424/60; 424/78
[58] Field of Search ............... 424/70, 60; 8/405, 425, 8/435

[56] References Cited

U.S. PATENT DOCUMENTS

| | | | |
|---|---|---|---|
| 2,848,369 | 8/1968 | Seemuller | 8/406 |
| 3,632,290 | 1/1972 | Tucker et al. | 8/425 X |
| 3,912,808 | 10/1975 | Sokol | 424/70 |
| 3,973,901 | 8/1976 | Micchelli et al. | 8/425 |
| 3,986,825 | 10/1976 | Sokol | 424/70 |
| 3,996,146 | 12/1976 | Tarasov | 424/70 |
| 4,223,009 | 9/1980 | Chakrabarti | 424/70 X |
| 4,299,817 | 11/1981 | Hannan, III et al. | 424/70 |

FOREIGN PATENT DOCUMENTS

| | | |
|---|---|---|
| 1221913 | 8/1983 | Canada . |
| 0089749 | 2/1983 | European Pat. Off. . |
| 0132960 | 6/1984 | European Pat. Off. . |
| 2138845A | 2/1984 | United Kingdom . |
| 2168082A | 7/1985 | United Kingdom . |

*Primary Examiner*—Ellis P. Robinson
*Assistant Examiner*—Susan S. Rucker
*Attorney, Agent, or Firm*—Gerard J. McGowan, Jr.

[57] ABSTRACT

An aqueous single phase composition, particularly for use in the treatment of keratinous fibres, comprises a cationic polymer or mixtures thereof, an anionic monomer or mixtures thereof, and a solubilizing agent chosen from amphoteric detergent active compounds, inorganic electrolytes and mixtures thereof. The composition should have an anionic to cationic charge ratio of from 0.2 to 1.0. When the monomer is an anionic dye, the composition can be employed in the dyeing of hair.

14 Claims, No Drawings

TREATMENT OF KERATINOUS FIBRES

This is a continuation of Ser. No. 074,838, filed July 17, 1987, now abandoned.

FIELD OF INVENTION

The invention relates to compositions for treating keratinous fibres, and more particularly to compositions for dyeing hair. For the sake of clarity, the following description will be concerned with the dyeing of human hair, although it is to be understood that the composition according to the invention can be employed in the treatment of other keratinous fibres, such as wool or animal fur, in order to dye them or to impart other benefits.

BACKGROUND & PRIOR ART

A problem with many hair dyes is that they cannot be quickly or easily removed from the hair. Permanent dyes can only be removed by bleaching which can damage the hair. Semi-permanent dyes, which penetrate the hair and are capable of giving deep shades, can last up to ten washes with a shampoo after application. Temporary dyes which do not penetrate the hair and which are removed by washing, suffer from several disadvantages. For example, the effect obtained from a rinse-off product is usually slight and is therefore regarded by the consumer as poor value. The depth of color using a temporary dyes can, however, be improved if employed as a leave-on product, but such products are not always fast to water and can rub off onto bedding, causing pillow staining. Hair spray products containing pigments and resins tend to fall off the hair and, for this reason, have not achieved popularity amongst consumers.

Accordingly, there exists a need for a temporary hair dye which is entirely safe to use, simple to apply, rapid in its effect, does not rub off onto bedding and which does not wash off the hair when contacted with water, such as in a rain shower, but which can nevertheless be removed by shampooing to enable a different color or shade to be applied as desired.

It has been proposed in U.S. Pat. No. 3,912,808 (Gillette Company) to employ a composition for waving or straightening hair, which comprises an aqueous solution of a reducing agent, a water-soluble cationic polymer having a molecular weight of from 20,000 to 3,000,000, such as polydiallyldiethylammonium chloride. Optionally, there can also be present in such compositions an amphoteric surfactant, for example, an imidazoline derivative made by condensing polyamines with long chain fatty acids, as well as an acidic, basic, or disperse dye or oxidation dye intermediate. It is however stipulated that when a surface active agent is present in the composition, there must also be present a water-miscible hydroxylated organic primarily aliphatic solvent, such as ethanol, isopropanol or benzyl alcohol.

We have now discovered that hair can be colored temporarily such that the dye applied thereto will be fast to water, but which can be removed by shampooing, by employing a composition which includes a polymer having a relatively high cationic charge and a monomer such as a dye having an anionic charge, preferably also with an amphoteric surfactant and/or a relatively high concentration of an inorganic electrolyte salt, as solubilising agents. Such a composition forms a single liquid phase solution which on dilution with water, such as during application to hair following shampooing forms an insoluble complex of the polymer and dye which adsorbs strongly to hair.

In comparative tests, to be described in detail later in this specification, it is apparent that a far more intense coloration of blonde hair is obtained following application of the composition according to the invention, than when a comparative composition based on the teaching of the Gillette U.S. Pat. No. 3,912,808 is employed.

DEFINITION OF THE INVENTION

According to the invention there is provided an aqueous single phase composition, particularly for use in the treatment of keratinous fibres, which comprises:

(i) from 0.1 to 10% by weight of a cationic polymer or mixtures thereof;

(ii) from 0.01 to 10% by weight of an anionic monomer or mixtures thereof;

(iii) a solubilising agent chosen from amphoteric detergent active compounds, inorganic electrolytes and mixtures thereof, provided that when the solubilising agent is an amphoteric detergent active compound, it forms from 0.1 to 20% by weight of the composition, and when the solubilising agent is an electrolyte, it forms from 1 to 30% by weight of the composition;

the composition having an anionic to cationic charge ratio of from 0.2 to 1.0.

DISCLOSURE OF THE INVENTION

The cationic polymer

The composition according to the invention comprises a cationic polymer preferably having a cationic charge density of at least 0.001. The cationic polymer may be a copolymer having the above characteristics, or it may be a random copolymer having charged regions which are block in nature, and which regions have the above characteristics.

"Charge density" as the term is used herein refers to the ratio of the number of charges on a polymer unit to the molecular weight of said polymer unit.

Preferably, the cationic polymer as a whole has a charge density of at least 0.004.

Particularly suitable cationic polymers are: poly(dimethyldiallylammonium chloride), having a cationic charge density of about 0.008, an example of which polymer has the CTFA designation Quaternium 40, and is for example available commercially as a 40% aqueous solution under the trade name MERQUAT 100 from the Merck Chemical Division of Merck & Co. Inc. USA; and poly(dimethylbutanylammonium chloride) -α, ω- bis (triethanolammonium chloride), having a cationic charge density of 0.01, an example of which polymer has the CTFA designation Quaternium 57, and is for example available commercially under the trade name ONAMER M from the Onyx Chemical Co. USA and is described in U.S. Pat. No. 4,027,020.

Further examples of suitable cationic polymers include:

MIRAPOL A-15, a high molecular weight polymeric quaternary ammonium chloride having the CTFA designation Polyquaternium -2, available from The Miranol Chemical Co Inc.

N.A.R.WT 20UHV, a very high molecular weight polydimethyl dialkyl ammonium chloride and N.A.R.78-4396, a low molecular weight dimethyl diallyl ammonium chloride, each having a charge density of about 0.008, and available from National Adhesives and Resins. LUVIQUAT FC 905, a copolymer of vinyl pyrrolidone and vinylimidazole quaternised with methyl chloride (1:19), having a charge density of 0.009, and available from BASF;

poly (dipropyldiallylammonium chloride); poly (methyl- -propaniodiallylammonium chloride); poly (diallylpiperidinium chloride); poly (vinylpyridinium chloride); quaternised poly (vinyl alcohol); quaternised (dimethylaminoethylmethacrylate) the degree of quaternisation of the respective polymers being such as to impart a charge density of at least 0.003.

Examples of suitable non-quaternary cationic polymers are:

POLYMER QR 686, an imidazoline acetate derivative available from Rohm & Haas;

CARTARETIN K, a cross-linked polyamidepolyamine available from Sandos

FLOC AID 311, a copolymer of acrylamide and diethyl ethylamino methacrylate (1:1) having a charge density of 0.0034 and available from GAF;

poly (n-vinylpyrrolidone); poly (dimethylaminoethylmethacrylate); poly (vinylpyridine); and poly (ethyleneimine).

Each of these non-quaternary cationic polymer also has a charge density of at least 0.003. It is possible to employ any one cationic polymer having an appropriate cationic charge density, as herein defined, or alternatively it is possible to employ two or more cationic polymers such as those exemplified above, or any other, provided that the net cationic charge density is at least 0.003

Copolymers of any of the above with other monomers such as, for example, acrylamide, diacetone acrylamide and styrene may also be used provided the charge density of the copolymer is at least 0.003.

The amount of cationic polymer to be employed in compositions according to the invention is generally from 0.1 to 10%, preferably from 0.5 to 10% and ideally from 0.5 to 2% by weight of the composition.

The anionic monomer

The composition according to the invention also comprises an anionic monomer which is capable of improving or protecting keratinous fibres. Examples of anionic monomers are anionic dyes and sunscreen agents.

The anionic dye

The composition according to the invention can comprise a water-soluble anionic dye, preferred examples of which are food dyes in view of their proven safety in use.

Particularly suitable anionic dyes are:

Food Black 1 (CI No. 28440), molecular weight 868, supplied by Butterfields under the trade name BLACK PN.

Acid Black 1 (CI No. 20470), molecular weight 612, supplied by Bayer under the trade name ACIDERM BLACK E108B Acid Black 2 (CI No. 50420), supplied by Bayer under the trade name NIGROSIN WLF.

Food Red 10 (CI No. 18050), molecular weight 509, supplied by Butterfields under the trade name DALFCOL RED 2G.

Food Blue 1 (CI No. 73015), molecular weight 467, supplied by Butterfields under the trade name DALFCOL INDIGO CARMINE.

Food Brown 3 (CI No.20285), supplied by L J Ponting & Sons Ltd under the trade name, BROWN HT Food Red 3 (CI No.14720), supplied by Williams (Hounslow) Ltd under the trade name CARMOISINE GRN Food Red 7 (CI No. 16255), supplied by Williams (Hounslow) Ltd under the trade name PONCEAU 4R Food Yellow No.4 (CI No. 19140), supplied by Drake-Law Laboratories under the trade name TARTRAZINE Food Yellow No.13 (CI No.47005), supplied by Butterfields under the trade name QUINOLINE YELLOW.

It is possible to employ a mixture of one or more anionic dyes, such as those exemplified above.

The total amount of anionic dye to be employed in compositions according to the invention is generally from 0.01 to 10%, preferably from 0.5 to 5% by weight of the composition.

The anionic sunscreen agent

The composition according to the invention can comprise an anionic sunscreen agent, or mixtures thereof.

The sunscreen agent when deposited thereon can protect keratinous fibres, particularly human hair, against the adverse effects of exposure to sunlight, such as fibre damage and bleaching.

Particularly suitable anionic sunscreen agents are p-methoxycinnamic acid salts, such as PARSOL HYDRO, available from Givaudin, and the sodium salt of phenyl benzimidazole-5-sulphate, such as EUSOLEX 232, available from Merck.

The solubilising agent

The composition according to the invention also comprises a solubilising agent chosen from amphoteric detergent active compounds, inorganic electrolytes and mixtures thereof.

The function of the solubilising agent is to ensure that the cationic polymer and the anionic monomer present in the composition are held in solution in the composition to maintain its single liquid phase character and do not prematurely form a precipitate, for it is not until the composition is ultimately used, for example in the dyeing of hair, that dilution with water causes a soluble complex formed between polymer and monomer, in this case the anionic dye, to precipitate onto the hair being dyed.

Although it is possible to use either an amphoteric detergent active compound or an inorganic electrolyte as the solubilising agent, it is preferred to use a mixture of both.

The amphoteric surfactant

When the solubilising agent comprises an amphoteric surfactant, a particularly suitable example is a betaine having the structure:

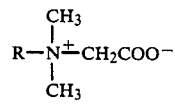

where R is R' or R";
R' is $C_{10}$-$C_{18}$ alkyl;
R" is R'CONH(CH$_2$)n; and
n is an integer of from 1 to 5.

Particularly preferred examples of suitable betaines include:

Lauryl/myristyl dimethyl betaine, such as EMPIGEN BB, and
Lauryl/stearyl-amidopropyl dimethyl betaine, such as EMPIGEN BT, available from Albright & Wilson Ltd.

The amphoteric surfactant can alternatively be an amine oxide or an alkyl-β-imino dipropionate.

The amount of amphoteric surfactant when employed in compositions according to the invention is generally from 0.1 to 20%, preferably from 1 to 5% by weight of the composition.

The inorganic electrolyte

When the solubilising agent comprises an inorganic electrolyte, particularly suitable examples are certain simple salts. These include the chlorides, bromides and nitrates of alkali metal salts, alkaline-earth metals and ammonium (including substituted ammonium salts). Specific examples of suitable salts are sodium chloride, sodium bromide, sodium nitrate, potassium chloride, potassium bromide, calcium chloride, magnesium chloride and ammonium chloride.

The amount of inorganic electrolyte when employed in compositions according to the invention is generally from 1 to 30%, preferably 5 to 15% by weight of the composition. It is to be understood, however, that the maximum amount of electrolyte will depend on its solubility in the composition and it is accordingly preferred that the composition does not contain a substantial excess of undissolved electrolyte.

Water

The composition according to the invention should also contain up to 99.79% by weight of water. Generally the water will form from 50 to 95%, preferably 60 to 90% by weight of the composition.

pH

The composition according to the invention should preferably have a pH value of from 5 to 7, most preferably from 6 to 6.5.

OPTIONAL INGREDIENTS

The composition according to the invention can optionally also comprise surfactants other than amphoteric surfactants, provided that when such optional ingredients are present, the composition possesses a net cationic charge.

Other surfactants

The composition according to the invention can optionally also include an anionic surfactant to provide the composition with hair conditioning benefits. Examples of anionic surfactants include alkyl sulphates, for example sodium lauryl sulphate, alkyl ether sulphates, for example sodium lauryl ether (2EO) sulphate and sodium lauryl ether (3EO) sulphate. Alkyl carboxylates, for example potassium laurate, aryl alkyl sulphonates, for example sodium dodecylbenzene sulphonate, dialkylsulphosuccinates, for example sodium di-octylsulphosuccinate, organic phosphate esters, for example sodium oleylether phosphates, dialkylsulphosuccinates, for example sodium di-N-lauryl sulphosuccinate, acylsarcosinates, for example sodium N-lauroyl sarconsinate, alkyl taurates, for example sodium N-methyl-N-oleyl taurate, and alkyl isethionates.

The amount of anionic surfactant that can optionally be employed in compositions according to the invention should not exceed that quantity which would result in the composition having a charge ratio of greater than 1. The composition should accordingly have a net cationic charge. The amount of anionic surfactant that can optionally be employed in compositions according to the invention is therefore generally from 0 to 10%, usually from 0.1 to 10% by weight of the composition.

Further optional ingredients

The composition according to the invention can also optionally contain further ingredients, of which a thickening agent, a perfume, and a preservative agent are examples. When a thickening agent is present in the composition according to the invention suitable examples are nonionic thickeners, such as, hydroxypropyl guar for example JAGUAR HP60, available from Meyhall. Ideally, the amount of hydroxypropyl guar that can be employed as a thickener in composition according to the invention should not exceed 2% by weight, otherwise the composition is likely to be inconveniently thick or viscous. An alternative nonionic thickener is PEG 6000 distearate.

When a perfume oil is included in the composition according to the invention, the perfume can be solubilised by the presence of a neutral surfactant such as the amphoteric surfactant referred to hereinbefore.

Charge ratio

It is an essential feature of the invention that the composition which will comprise both anionic species, including the anionic monomer, and cationic species, including the cationic polymer, will possess an anionic to cationic charge ratio of from 0.2 to 1.0. Preferably, this charge ratio is not greater than 0.7.

The change ratio is defined as follows:

$$\text{Charge ratio} = \frac{\text{Total number of moles of negative charges}}{\text{Total number of moles of positive charges}}$$

It has been shown that if the charge ratio of the anionic species to the cationic species is less than 1.0, then the anionic monomer and the cationic polymer form a complex which on dilution with water, separates from solution as an oily "precipitated" material appearing as small droplets, probably cationic in character, which coat the fibre evenly.

If, however, the said charge ratio is greater than 1.0, then there is a tendency for the anionic monomer and the cationic polymer to form a solid precipitate which is less substantive to the fibre and which can be dislodged leaving a poor, uneven coverage of the fibre. This is particularly evident when the anionic monomer is a dye which is used to dye human hair, compositions having a charge ratio of less than 1.0 permitting even dyeing of the hair, in contrast to compositions having a charge ratio of greater than 1.0 giving rise to poor, uneven dye coverage.

It is also important for adequate delivery of the anionic monomer to the keratinous fibre, that the charge ratio is not less than 0.2.

The calculation of the charge ratio is illustrated by reference to examples of preferred anionic dyes and a preferred cationic polymer as shown in the following table.

| Anionic dye | No of (+ or −) | Molecular weight | MW/ Charge | Moles of charges/g (× 10³)° |
|---|---|---|---|---|
| Food Black 1 | 4 (−) | 868 | 217 | 4.61 |
| Acid Black 1* | 2 (−) | 612 | 306 | 3.27 |
| Food Red 10 | 2 (−) | 509 | 255 | 3.93 |
| Sodium lauryl ether sulphate 3EO | 1 (−) | 418 | 418 | 2.39 |
| Cationic Polymer | | | | |
| MERQUAT 100+ | 1 (+) per monomer unit | 148 per monomer unit | 148 | 6.76 |

NOTES:

* Acid Black 1 also contains an amino group which at pH 6–6.5 may be partially protonated to yield a cationic species.

+ For the purpose of this calculation, the polymer is considered as a set of monomer units, each unit containing one charged group.

$$\text{Calculated as: } \frac{\text{No. of charges}}{\text{molecular weight}} \times 10^3$$

The following example illustrates the calculation of the charge ratio.

For a composition according to the invention comprising, for example, equal concentrations of Food Black 1 and MERQUAT 100, no other charged species being present, the charge ratio employing values taken from the above table for these two materials is:

$$\frac{4.6}{6.76} = 0.68$$

PROCESS FOR MANUFACTURE OF HAIR TREATMENT COMPOSITION

The invention also provides a process for the manufacture of the hair treatment composition according to the invention which process comprises the step of mixing together the oppositely charged ingredients, for example the anionic monomer such as dye or sunscreen and the cationic polymer in the presence of the solubilising agent chosen from the amphoteric detergent active compound or electrolyte or a mixture thereof and water.

According to a preferred process, an aqueous solution of amphoteric detergent active compound, electrolyte and cationic polymer is prepared first and to this is added with stirring an aqueous solution of the anionic monomer.

Alternatively, an aqueous solution of amphoteric detergent active compound, electrolyte and anionic monomer is prepared, and to this is added with mixing an aqueous solution of the cationic polymer.

PACKAGING OF THE COMPOSITION

The composition according to the invention can be packaged and stored prior to use in any convenient container.

Suitable containers include plastic sachets, capped bottles, pump spray operated applicators or pressurized aerosol canisters. Preferably the container is transparent or translucent so that the contents can be seen as a single liquid phase and, with multidose containers, so that a measured dose can more readily be dispensed.

METHOD OF DYEING HUMAN HAIR

The invention also relates to a method of dyeing human hair, either hair attached to the body or hair in the form of switches, hair pieces and wigs, which method comprises applying the aqueous composition according to the invention to wet hair and thereafter rinsing the hair with water. In this procedure, the composition is diluted with at least ten times it volume of water, and this results in the precipitation and deposition onto the hair of a complex formed between the cationic polymer and the anionic dye. The "precipitate" preferably present as an oily complex, is apparently strongly retained by the hair in view of the fact that hair normally possesses an anionic charge.

The hair can then be rinsed after application of the dye composition and subsequently set to a desired style as necessary and dried according to conventional procedures.

A similar method can be employed in the treatment of hair with an anionic sunscreen.

MEASUREMENT OF HAIR COLOR

In order to assess the color of hair dyed with compositions according to the invention, the reflectance spectra of hair switches were measured from 400–700nm in a Micromatch spectrophotometer in the absence of ultra-violet light. Color difference analysis from these data were made using computer programs.

Small switches of blond hair, each 10 cm in length and weighing 0.5 g were accommodated in the spectrophotometer using a holder with a narrow slit. Only switches in good condition with well aligned fibres were used. Due to the itinerant variance of hair, each switch was repositioned at least four times in the holder for multiple readings. An average value was used in calculating the color intensity.

The use of standards in the color analysis of hair is necessary as the perception of color cannot be measured directly and is dependent on:

(i) the visible reflectance spectrum (R $[\lambda]$),
(ii) the spectral energy distribution of the light source (S $[\lambda]$), and
(iii) the spectral sensitivity of the eye (x $[\lambda]$).

For consistency and comparability these last two need to be defined as standards.

The color space is defined by the tristimulus values X, Y and Z; thus:

$$X = K \sum_{400}^{700} R[\lambda] . S[\lambda] . x[\lambda]$$

and similarly for Y and Z. K is a factor which ensures that the maximum value of Y for any illuminant spectral distribution is 100.

Values of S [λ] and of x [λ] have been determined and are an integral part of the CIE 1976 standards. In the experiments to be described later in this specification, the illuminant $D_{65}$ for the 10° observer was used.

The values X, Y and Z give a non-uniform color space with respect to color perception. It is necessary, therefore, to transform them into the approximately uniform color space given by L, A and B, as defined by the CIELAB 76 formulae. These values are expressed in rectangular coordinates.

The L value is a measure of the brightness of the sample on a grey scale from white to black. The A and B values are measures of the color where;
+A is red
−A is green
+B is yellow
−B is blue The difference between two samples in the CIELAB space, usually a standard, is given by $$\Delta E = [(\Delta L)^2 + (\Delta A)^2 + (\Delta B)^2]^{\frac{1}{2}}$$

The compositions according to the invention containing an anionic dye as the anionic monomer, when employed in the dyeing of hair according to the procedure described herein using blond hair, will provide a color intensity (ΔE) value preferably of at least 25. Ideally, the color intensity (ΔE) value obtained is at least 30.

EXAMPLES

The following examples illustrate the invention.

Example 1

A single liquid phase clear hair dyeing composition had the following formulation:

|  | % w/w |
| --- | --- |
| MERQUAT 100 (40% solution) | 2.5 |
| Acid Black 1 (CI 20470) | 0.5 |
| EMPIGEN BB (30% solution) | 2.7 |
| Sodium Chloride | 12 |
| Water | to 100 |
| pH = 6.0 | |

The effect of this composition was tested by applying 0.25g of this formulation diluted with 2.25g water to blond hair switches (0.5g in weight and 10cm in length) for two minutes and then rinsing with water for 30 seconds and drying with a hair dryer.

The intensity of the blue color obtained was determined using the Micromatch spectrophotometer as described herein and the following LAB values were obtained:
L=51.3
A=−8.8
B=−2.8

From these values, the ΔE value was calculated as 31.4. This confirms a strong, intense blue color was obtained.

The invention is also illustrated by the following Examples 2 to 6. In each case, the single liquid phase hair dyeing composition was applied to switches of hair and color evaluated in the manner described in Example 1.

Example 2

| Ingredient | % w/w |
| --- | --- |
| Merquat 100 | 2.5 |
| Quinoline Yellow | 1.0 |
| Empigen BB | 12.0 |
| Sodium chloride | 3.0 |
| Water to | 100.0 |
| pH = 4.0 | |

This imparts a yellow color to the hair. The following L, A and B values were obtained using the Micromatch spectrophotometer.
L=71; A=2; B=50
From these values, the ΔE value was calculated as 29.

Example 3

| Ingredient | % w/w |
| --- | --- |
| Merquat 100 | 2.5 |
| Ponceau 4R | 1.0 |
| Empigen BB | 9.0 |
| Sodium chloride | 12.0 |
| Water to | 100.0 |
| pH = 4.0 | |

This imparts a pink-red color to the hair.
The following L, A and B values were obtained using the Micromatch spectrophotometer.
L=52; A=35; B=17
From these values, the ΔE value was calculated as 41.

Example 4

| Ingredient | % w/w |
| --- | --- |
| Mirapol A-15 | 4.5 |
| Black PN | 3.0 |
| Sodium chloride | 12.0 |
| Water to | 100.0 |

This imparts a dark blue color to the hair.
The following L, A and B values were obtained using the Micromatch spectrophotometer.
L=38.0; A=−2.6; B=−10.1
From these values, the ΔE value was calculated as 40.

Example 5

| Ingredient | % w/w |
| --- | --- |
| Merquat 100 | 1.25 |
| Black PN | 0.5 |
| SLES 3EO | 0.5 |
| Empigen BB | 4.5 |
| Jaguar HP60 | 1.0 |
| Sodium chloride | 12.0 |
| Water to | 100.0 |
| pH = 4.0 | |

This system imparts a blue color to the hair and also conditions the hair.
The following L, A and B values were obtained using the Micromatch spectrophotometer.
L=54; A=−5; B=−2
From these values, the ΔE value was calculated as 37.

Example 6

| Ingredient | % w/w |
| --- | --- |
| Merquat 100 | 3.0 |
| Briphos 03D | 0.75 |
| Black PN | 0.38 |
| Brown HT | 0.38 |
| Empigen BB | 7.8 |
| Sodium chloride | 9.0 |
| Jaguar HP-60 | 1.0 |
| Water to | 100.0 |

This imparts a brown color to the hair and also conditions the hair.

The following L, A and B values were obtained using the Micromatch spectrophotometer.
L=51; A=1.2; B=6.0
From these values, the ΔE was calculated as 27.

The invention is also illustrated by the following Examples 7 and 8 which are directed to compositions for treating hair to apply thereto sunscreen agents.

Example 7

| Ingredient | % w/w |
| --- | --- |
| Merquat 100 | 2.0 |
| Parsol Hydro | 1.0 |
| Empigen BB | 8.0 |
| Sodium chloride | 10.0 |
| Water to | 100.0 |

Example 8

| Ingredient | % w/w |
| --- | --- |
| Merquat 100 | 2.5 |
| Eusolex 232 | 1.5 |
| Empigen BB | 9.0 |
| Sodium chloride | 12.0 |
| Water | 100.0 |

COMPARATIVE EXPERIMENT

An experiment was performed to compare the color obtained using the system described in Example 17 of Gillette U.S. Pat. No. 3,912,808, with that obtained using compositions according to the invention.

(a) Gillette U.S. Pat. No. 3,912,808, Example 17

The following formulations were prepared to evaluate the ability of the Example 17, and similar formulations in which the cationic polymer was omitted, to color blond hair. One alternative anionic dye was also employed by was of comparison. The formulations contained the following ingredients:

| Ingredients: | % by weight Formulations No. | | | |
| --- | --- | --- | --- | --- |
| | 1 | 2 | 3 | 4 |
| MIRANOL C2M conc. | 8.0 | 8.0 | 8.0 | 8.0 |
| MERQUAT 100 | 5.0 | — | 5.0 | — |
| Food Blue No. 1 | 0.5 | 0.5 | — | — |
| Acid Black No. 1 | — | — | 0.5 | 0.5 |
| Benzyl alcohol | 4.5 | 4.5 | 4.5 | 4.5 |
| Water to | 100 | 100 | 100 | 100 |

[Note: Formulation No. 1 corresponds precisely to Example 17 of U.S. Pat. No. 3,912,808, Food Blue No1, being a more recent name for the anionic dye F D & C Blue No2.]

Blond hair switches were treated with each formulation as described in Example 1 and the L A and B values measured. From these, ΔE values were calculated and the results are shown below:

| Formulation No. | L | A | B | ΔE |
| --- | --- | --- | --- | --- |
| 1 | 69.1 | −3.4 | 8.4 | 8.3 |
| 2 | 71.0 | −1.6 | 12.7 | 3.6 |
| 3 | 55.4 | −4.7 | 0.7 | 15.9 |
| 4 | 72.9 | −1.9 | 12.4 | 4.0 |
| Untreated (blond control) | 73.1 | 1.2 | 17.1 | 0.0 |

(b) Compositions according to the invention

The following formulations were prepared to compare the effect of using different concentrations of anionic dye, and also to confirm the advantage of employing a relatively high concentration of electrolyte (sodium chloride). These formulations contained the following ingredients:

| Ingredient: | % by weight Formulation No. | | |
| --- | --- | --- | --- |
| | 5 | 6 | 7 |
| EMPIGEN BB | 0.9 | 0.9 | 0.9 |
| MERQUAT 100 | 1.0 | 1.0 | 1.0 |
| Acid Black 1 | 0.5 | 1.0 | 2.0 |
| Sodium chloride | 12.0 | 12.0 | 12.0 |
| Water to | 100 | 100 | 100 |

Blond hair switches were treated with each formulation as described in Example 1 and the L A and B values measured. From these, ΔE values were calculated and the results are shown below:

| Formulation | L | A | B | ΔE |
| --- | --- | --- | --- | --- |
| 5 (Example 1) | 51.3 | −8.8 | −2.8 | 31.4 |
| 6 | 37.3 | −3.1 | −7.1 | 44.1 |
| 7 | 29.3 | −0.4 | −3.1 | 49.2 |

The results of this comparative experiment show that although blond hair dyed with a formulation containing both an anionic dye and a cationic polymer having a relatively high charge density will attain a color which is just discernible (e.g. ΔE of 15.9 as shown for example with Formulation 3), the presence of an electrolyte at a relatively high concentration, in addition to an amphoteric detergent active compound as shown for example with Formulations 5, 6 & 7, each in accordance with the invention, is preferable in order to obtain a substantial Color. This can be seen from the ΔE values all of which exceed 30. It is also apparent that formulations containing no cationic polymer (i.e. Formulations 2 and 4) did not result in a color that was perceivable, as shown by the very low ΔE values of 3.6 and 4.0 respectively which were obtained.

The poor dyeing performance of Example 17 (Formulation 1) in this comparative experiment can be explained by the fact that its natural pH is 8.3, and that because of this, some of the dye precipitated out of solution to form a phase-separated system unlike the single phase system of the composition according to the invention.

In a further experiment, the pH value of Example 17 (Formulation 1) was reduced by the addition of acid from 8.3 to a value of 5.5 and a single phase resulted, the dye ingredients then being completely dissolved in the formulation. This pH modified Formulation 1 then had an anionic : cationic charge ratio of 0.16 which was too low to provide adequate dyeing of hair switches.

It was concluded from these experiments that U.S. Pat. No. 3,912,808 did not teach aqueous single phase compositions for use in the dyeing of keratinous fibres, nor did it teach compositions which were capable of dyeing grey or blond hair to a significant intensity as judged by the ΔE values obtained in the above experimental comparisons.

We claim:

1. An aqueous, substantially organic solvent-free single phase composition, suitable for use in the treatment of keratinous fibres, which comprises:
   (i) from 0.1 to 10% by weight of a cationic polymer having a cationic charge density of at least 0.001 selected from the group consisting of:
   poly (dimethyldiallylammonium chloride);
   poly (dimethylbutanylammonium chloride)-60 , ω-bis (triethanolammonium chloride)
   poly (dipropyldiallylammonium chloride);
   poly (methyl-β-propaniodiallyl ammonium chloride);
   poly (diallylpiperidinium chloride);
   poly (vinylpyridinium chloride);
   quaternised poly (vinyl alcohol);
   quaternised (dimethylaminoethylmethacrylate);
   poly (n-vinyl pyrrolidone);
   poly (dimethylaminoethylmethacrylate);
   Polyquaternium - 2;
   poly (vinylpyridine);
   poly (ethyleneimine);
   and mixtures thereof;
   (ii) from 0.01 to 10% by weight of an anionic monomer selected from the group consisting of anionic dyes, anionic sunscreen agents, and mixtures thereof;
   (iii) from 0.1 to 20% by weight of amphoteric detergent active compound;
   (iv) from 1 to 30% by weight of an inorganic electrolyte selected from the group consisting of alkali metal, alkaline earth metal, ammonium and substituted ammonium, -chlorides, -bromides, -nitrates, the composition having an anionic to cationic charge ratio of from 0.2 to 1.0.

2. The composition of claim 1, wherein the anionic monomer is an anionic dye selected from the group consisting of Food Black 1, Acid Black 1, Acid Black 2, Food Red 10, Food Blue 1, Food Brown 3, Food Red 3, Food Red 7, Food Yellow No. 4, Food Yellow No. 13 and mixtures thereof.

3. The composition of claim 1, wherein the anionic monomer is an anionic sunscreen agent selected from the group consisting of p-methoxycinnamic salts, sodium salt of phenyl benzimidazole-5-sulfate and mixtures thereof.

4. The composition of claim 1, wherein the amphoteric detergent active compound is a betaine having the structure:

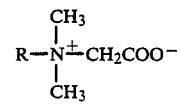

where R is R' or R";
R' is $C_{10}$–$C_{18}$ alkyl;
R" is R'CONH (CH$_2$)n; and
n is an integer of from 1 to 5.

5. The composition of claim 4, wherein the betaine is selected from the group consisting of lauryl/myristyl dimethyl betaine, lauryl/stearyl-amidopropyl dimethyl betaine and mixtures thereof.

6. The composition of claim 1, wherein the a pH value of the composition is between 5 and 7.

7. An aqueous, single phase composition, suitable for use in the treatment of keratinous fibres, which comprises:
   (i) from 0.1 to 10% by weight of a cationic polymer having a cationic charge density of at least 0.001 selected from the group consisting of:
   poly (dimethyldiallylammonium chloride);
   poly (dimethylbutanylammonium chloride)-α, ω-bis (triethanolammonium chloride)
   poly (dipropyldiallylammonium chloride);
   poly (methyl-β-propaniodiallyl ammonium chloride);
   poly (diallylpiperidinium chloride);
   poly (vinylpyridinium chloride);
   quaternised poly (vinyl alcohol);
   quaternised (dimethylaminoethylmethacrylate);
   poly (n-vinyl pyrrolidone);
   poly (dimethylaminoethylmethacrylate);
   Polyquaternium - 2;
   poly (vinylpyridine);
   poly (ethyleneimine);
   and mixtures thereof;
   (ii) from 0.01 to 10% by weight of an anionic monomer selected from the group consisting of anionic dyes, anionic sunscreen agents, and mixtures thereof;
   (iii) from 0.1 to 20% by weight of amphoteric detergent active compound;
   (iv) from 5 to 30% by weight of an inorganic electrolyte selected from the group consisting of alkali metal, alkaline earth metal, ammonium and substituted ammonium, -chlorides, -bromides, -nitrates, the composition having an anionic to cationic charge ratio of from 2.0 to 1.0.

8. The composition of claim 7, wherein the anionic monomer is an anionic dye selected from the group consisting of Food Black 1, Acid Black 1, Acid Black 2, Food Red 10, Food Blue 1, Food Brown 3, Food Red 3, Food Red 7, Food Yellow No. 4, Food Yellow No. 13 and mixtures thereof.

9. The composition of claim 3, wherein the anionic monomer is an anionic sunscreen agent selected from the group consisting of p-methoxycinnamic salts, sodium salt of phenyl benzimidazole-5-sulfate and mixtures thereof.

10. The composition of claim 7, wherein the amphoteric detergent active compound is a betaine having the structure:

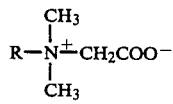

where R is R' or R";
R' is $C_{10}$–$C_{18}$ alkyl;
R" is R'CONH $(CH_2)n$; and
n is an integer of from 1 to 5.

11. The composition of claim 10, wherein the betaine is selected from the group consisting of lauryl/myristyl dimethyl betaine, lauryl/stearyl-amidopropyl dimethyl betaine and mixtures thereof.

12. The composition of claim 7 wherein the pH value of the composition is between 5 and 7.

13. The composition of claim 7 wherein the level of electrolyte is from 5 to 15%.

14. An aqueous, single phase composition, suitable for use in the treatment of keratinous fibres, and including a solubilizing agent which consists essentially of amphoteric detergent, active, inorganic electrolyte and water, which comprises:
(i) from 0.1 to 10% by weight of a cationic polymer having a cationic charge density of at least 0.001 selected from the group consisting of:
poly (dimethyldiallylammonium chloride);
poly (dimethylbutanylammonium chloride)-α, ω-bis (triethanolammonium chloride)
poly (dipropyldiallylammonium chloride);
poly (methyl-β-propaniodiallyl ammonium chloride);
poly (diallylpiperidinium chloride);
poly (vinylpyridinium chloride);
quaternised poly (vinyl alcohol);
quaternised (dimethylaminoethylmethacrylate);
poly (n-vinyl pyrrolidone);
poly (dimethylaminoethylmethacrylate);
Polyquaternium - 2;
poly (vinylpyridine);
poly (ethyleneimine);
and mixtures thereof;
(ii) from 0.01 to 10% by weight of an anionic monomer selected from the group consisting of anionic dyes, anionic sunscreen agents, and mixtures thereof;
(iii) from 0.1 to 20% by weight of amphoteric detergent active compound;
(iv) from 1 to 30% by weight of an inorganic electrolyte selected from the group consisting of alkali metal, alkaline earth metal, ammonium and substituted ammonium, -chlorides, -bromides, -nitrates, the composition having an anionic to cationic charge ratio of from 0.2 to 1.0.

* * * * *